(12) United States Patent
Larsson

(10) Patent No.: US 11,547,784 B2
(45) Date of Patent: Jan. 10, 2023

(54) SYSTEM FOR CO2 REMOVAL

(71) Applicant: MAQUET CRITICAL CARE AB, Solna (SE)

(72) Inventor: Ake Larsson, Jarfalla (SE)

(73) Assignee: MAQUET CRITICAL CARE AB, Solna (SE)

( * ) Notice: Subject to any disclaimer, the term of this patent is extended or adjusted under 35 U.S.C. 154(b) by 443 days.

(21) Appl. No.: 16/466,501

(22) PCT Filed: Dec. 8, 2016

(86) PCT No.: PCT/SE2016/051231
§ 371 (c)(1),
(2) Date: Jun. 4, 2019

(87) PCT Pub. No.: WO2018/106164
PCT Pub. Date: Jun. 14, 2018

(65) Prior Publication Data
US 2019/0344005 A1    Nov. 14, 2019

(51) Int. Cl.
*A61M 5/00* (2006.01)
*A61M 1/16* (2006.01)
(Continued)

(52) U.S. Cl.
CPC ......... *A61M 1/1698* (2013.01); *A61B 5/0803* (2013.01); *A61B 5/369* (2021.01);
(Continued)

(58) Field of Classification Search
CPC ....... A61B 5/021; A61B 5/0836; A61B 5/087; A61B 5/14542; A61B 5/4836;
(Continued)

(56) References Cited

U.S. PATENT DOCUMENTS

2015/0034082 A1* 2/2015 Kimm ................ A61B 5/14542
128/202.16
2015/0231351 A1* 8/2015 Jonson ................ A61B 5/4836
128/204.22

FOREIGN PATENT DOCUMENTS

CN      102500004    6/2012
GB       2437254    10/2007
(Continued)

OTHER PUBLICATIONS

Luo YM, Moxham J, Polkey MI. Diaphragm electromyography using an oesophageal catheter: current concepts. Clin Sci (Lond). Oct. 2008;115(8):233-44. doi: 10.1042/CS20070348. PMID: 18782085. (Year: 2008).*

*Primary Examiner* — Allison G Fitzsimmons
(74) *Attorney, Agent, or Firm* — Fay Kaplun & Marcin, LLP

(57) ABSTRACT

A system for carbon dioxide (CO2) removal from a circulatory system of a patient includes a medical device providing extracorporeal lung assist (ECLA) treatment to the patient through extracorporeal removal of CO2 from the patient's blood; at least one control unit controlling the operation of the medical device so as to control a degree of CO2 removal obtained by the ECLA treatment; and a bioelectric sensor detecting a bioelectric signal indicative of the patient's efforts to breathe. The at least one control unit is configured to control the operation of the medical device based on the detected bioelectric signal.

16 Claims, 5 Drawing Sheets

(51) Int. Cl.
    *A61M 16/00*    (2006.01)
    *A61B 5/08*    (2006.01)
    *A61B 5/00*    (2006.01)
    *A61B 5/369*    (2021.01)
    *A61B 5/389*    (2021.01)
    *B01D 29/00*    (2006.01)
    *A61M 1/32*    (2006.01)
    *A61M 1/36*    (2006.01)

(52) U.S. Cl.
    CPC ............ *A61B 5/389* (2021.01); *A61B 5/4848* (2013.01); *A61B 5/6814* (2013.01); *A61B 5/7282* (2013.01); *A61M 16/026* (2017.08); *A61B 5/6823* (2013.01); *A61B 2505/03* (2013.01); *A61M 1/32* (2013.01); *A61M 1/3666* (2013.01); *A61M 2016/0027* (2013.01); *A61M 2205/3569* (2013.01); *A61M 2205/3592* (2013.01); *A61M 2230/42* (2013.01)

(58) Field of Classification Search
    CPC .. A61M 16/005; A61M 16/16; A61M 16/204; A61M 16/205; A61M 2016/0021; A61M 2016/0027; A61M 2016/0036; A61M 2016/0039; A61M 2016/0042; A61M 2016/103; A61M 2205/18; A61M 2205/3561; A61M 2205/3569; A61M 2205/3592; A61M 2205/50; A61M 2230/205; A61M 2230/30; A61M 2230/432; A61M 2230/46; A61M 16/0003; A61M 16/0069; A61M 16/026; A61M 16/085; A61M 2016/0015; A61M 2016/003; A61M 2205/3334; A61M 2205/60

See application file for complete search history.

(56) References Cited

FOREIGN PATENT DOCUMENTS

| WO | 2010/040656 | 4/2010 |
|---|---|---|
| WO | 2011/021978 | 2/2011 |
| WO | 2016/060596 | 4/2016 |

\* cited by examiner

SYSTEM FOR CO2 REMOVAL

TECHNICAL FIELD

The present invention pertains to the field of intensive care equipment for oxygenation and carbon dioxide (CO2) removal of blood in critically ill patients. In particular, the present invention relates to a medical device for providing extracorporeal lung assist (ECLA) treatment to a patient through extracorporeal removal of CO2 from the patient's blood, and to a system including such a medical device. The invention also relates to a method for extracorporeal removal of CO2 from the patient's blood.

BACKGROUND

Ventilators and medical devices for extracorporeal removal of CO2 from human blood are well known examples of intensive care equipment that are used to provide ventilatory and sometimes circulatory support to patients with reduced lung function.

Ventilators are used to provide respiratory treatment to patient's through the supply of oxygen-containing breathing gas to the patient's lungs, allowing CO2 to be removed from, and oxygen to be added to, the circulatory system of a patient through gas exchange within the lungs.

Medical devices for extracorporeal removal of CO2 from human blood, for example heart-lung machines and extracorporeal membrane oxygenation (ECMO) machines, are primarily used to provide ventilatory and circulatory support to patients having reduced lung and/or heart function in situations where conventional and less invasive treatments, such as mechanical ventilation, are insufficient. In general, such a medical device mimics the function of the lungs or both the heart and lungs. Carbon dioxide rich blood flows from the patient and is pumped to an extracorporeal oxygenator which serves as an artificial lung by removing CO2 and adding oxygen to the blood before the oxygen-enriched blood is returned to the circulatory system of the patient. A treatment allowing CO2 to be removed from the circulatory system of a patient as part of extracorporeal oxygenation of a machine-generated flow of blood will herein be referred to as an extracorporeal lung assist treatment (ECLA). Likewise, a medical device adapted to provide ECLA treatment to a patient will hereinafter be referred to as an ECLA device. In medicine literature, ECLA treatment may also be referred to as extracorporeal carbon dioxide removal (ECCO2R). In more extreme situations where the entire carbon dioxide/oxygen gas exchange takes place extracorporeal to the patient, the treatment is sometimes referred to as extracorporeal membrane oxygenation (ECMO).

One problem associated with respiratory treatments of patients suffering from severe reduction in lung capacity is the relatively large tidal volumes and high airway pressures required for sufficient ventilation of the patient's lungs. High-intensity ventilation with large tidal volumes and/or high pressures may injure the pulmonary system of the patient.

One problem associated with ECLA treatments is that, in order to generate a sufficient flow of blood through the ECLA device, large vessels (veins and arteries) are required for cannulation and large cannulae and tubes are required for transport of blood. This makes the procedure of connecting the patient to an ECLA device critical, often requiring the attention of a specialized vascular surgeon.

In the prior art, it has been suggested to coordinate ECLA and respiratory treatments to overcome some of the above mentioned problems.

WO 2011/021978 A1 presents a ventilatory support system wherein a ventilator and an ECLA device (referred to as "lung assist device") are made to cooperate such that an effective and non-injurious overall treatment can be provided to a patient who is connected to both the ventilator and the ECLA device. This is achieved by controlling the operation of the ECLA device based on a control parameter that is obtained by the ventilator, or vice versa. For example, in one embodiment, a measure of end-tidal carbon dioxide (EtCO2) in the expiration gases exhaled by the patient, obtained by the ventilator, is used as control parameter for controlling the operation of the ECLA device.

Also in more conventional ECLA devices, a parameter indicative of EtCO2 or any other measure of the CO2 content in expiration gas exhaled by the patient, or in the extracorporeal blood flow downstream of the oxygenator of the ECLA device, may be used to control the operation of the ECLA device in order to control the degree of CO2 removal from the patient's blood. Most often, the operation of the ECLA device is manually controlled by an operator based on a monitored measure of said parameter.

SUMMARY

The present invention relates to controlling a medical device for extracorporeal removal of CO2 from human blood, i.e., an ECLA device, from conventional control technologies relying on EtCO2 or other expired CO2 indicating parameters.

According to one aspect of the present disclosure there is provided a medical device for providing ECLA treatment to a patient through extracorporeal removal of CO2 from the patient's blood, i.e. an ECLA device, comprising a control unit for controlling the operation of the ECLA device so as to control a degree of CO2 removal achieved through the ECLA treatment. The control unit is configured to control the operation of the ECLA device based on a bioelectric signal indicative of the patient's efforts to breathe, so as to control the degree of extracorporeal CO2 removal in response to the breathing efforts of the patient.

According to another aspect of the present disclosure there is provided a system for CO2 removal from the circulatory system of a patient, comprising an ECLA device and at least one control unit for controlling the operation of the ECLA device so as to control a degree of CO2 removal achieved through the ECLA treatment. The system further comprises a bioelectric sensor for detecting a bioelectric signal indicative of the patient's efforts to breathe, wherein the at least one control unit is configured to control the operation of the ECLA device based on the detected bioelectric signal.

By controlling the ECLA device based on a bioelectric signal that indicates the patient's efforts to breathe, and thus the respiratory drive of the patient, the operation of the ECLA device can be automatically and instantly controlled to adapt the degree of extracorporeal removal of CO2 to the current need for CO2 removal as indicated by the respiratory drive of the patient.

In one exemplary embodiment, the at least one control unit is configured to automatically intensify the operation of the ECLA device when the bioelectric signal indicates that a current degree of CO2 removal is insufficient. The bioelectric signal may be a signal having an amplitude that is proportional to the patient's effort to breath. If the amplitude of the bioelectric signal is high, or if the amplitude of the bioelectric signal increases over time, the at least one control unit may be configured to intensify the operation of the ECLA device to reduce the high or increasing demand for air by the patient.

The ECLA device may advantageously be set-up to cooperate with a ventilator for providing respiratory treatment to the patient through the supply of breathing gas to the patient's lungs, in addition to the ECLA treatment provided by the ECLA device. In this situation, the at least one control unit may be configured to control the operation of the ECLA device based on both the bioelectric signal and a current level of ventilation of the patient, provided by the ventilator.

The current level of ventilation of the patient may be determined by the at least one control unit from any of, or any combination of, a tidal volume of breathing gas delivered to the patient, a peak pressure of breathing gas delivered to the patient, and a bodyweight of the patient. In one exemplary embodiment, the at least one control unit is configured to determine the current level of ventilation of the patient from parameters including the tidal volume of breathing gas currently being delivered to the patient and the bodyweight of the patient. The tidal volume and/or peak pressure used to determine the current level of ventilation of the patient may be set values that are manually set by an operator of the ventilator, or actual values that are determined from flow, volume and/or pressure measurements obtained by sensors in the ventilator or the breathing circuit connecting the patient to the ventilator.

For example, the at least one control unit may be configured to compare a parameter indicative of the current level of ventilation of the patient with a threshold value indicative of a maximum level of ventilation of the patient, and to control the operation of the ECLA device based on the bioelectric signal and the result of the comparison.

In one exemplary embodiment, the at least one control unit is configured to control the ECLA device so as to increase the degree of $CO_2$ removal obtained by the ECLA treatment when the bioelectric signal indicates that a total degree of $CO_2$ removal obtained by the ECLA treatment and the respiratory treatment is insufficient, and the current level of ventilation substantially corresponds to, or exceeds, a maximum level of ventilation of the patient. The maximum level of ventilation may be a maximum tidal volume and/or a maximum peak pressure, such as an estimated maximum clinically tolerable tidal volume or peak pressure for the specific patient and condition, estimated based on actual or predicted body weight of the patient.

In this way, the ECLA device can be operated as a slave to the ventilator in a master-slave configuration in which the ECLA device is operated at low intensity as long as the bioelectric signal and the current level of ventilation indicate that a sufficient degree of $CO_2$ removal is obtained at a non-injurious level of ventilation.

The ECLA device may advantageously be set-up to cooperate with a NAVA (neurally adjusted ventilatory assist) enabled ventilator for providing NAVA treatment to the patient in addition to the ECLA treatment provided by the ECLA device. In this situation, the operation of both the ventilator and the ECLA device can be controlled based on the bioelectric signal detected by the bioelectric sensor. Controlling the ECLA device and the ventilator based on the same bioelectric signal provides for direct coupling between the ECLA device and the ventilator, and instant adjustment of the ECLA treatment and the respiratory treatment to the patient's need for $CO_2$ removal. Another advantage of controlling the operation of the ECLA device based on the bioelectric signal used for controlling the operation of NAVA-enabled ventilators is that this signal is readily available at the bedside of critically ill patients being subjected to NAVA treatment.

Thus, the proposed system for $CO_2$ removal may, in addition to the ECLA device, further comprise a ventilator for providing respiratory treatment to the patient through the supply of breathing gas to the patient's lungs, wherein the at least one control unit of the system is configured to control the operation of both the ECLA device and the ventilator based on the bioelectric signal detected by the bioelectric sensor.

In this scenario, the at least one control unit may be configured to, when the bioelectric signal indicates that a total degree of $CO_2$ removal obtained by the ECLA treatment and the respiratory treatment is insufficient, control the ventilator so as to increase the degree of $CO_2$ removal obtained by the respiratory treatment if the current level of ventilation is below the maximum level of ventilation of the patient, and to control the ECLA device so as to increase the degree of $CO_2$ removal obtained by the ECLA treatment if the current level of ventilation substantially corresponds to, or exceeds, the maximum level of ventilation of the patient.

In another scenario, the at least one control unit may be configured to, when the bioelectric signal indicates that a total degree of $CO_2$ removal obtained by the ECLA treatment and the respiratory treatment is insufficient, control the ventilator so as to increase the degree of $CO_2$ removal obtained by the respiratory treatment if the current level of ventilation is below a threshold level of ventilation of the patient, and to control the ECLA device so as to increase the degree of $CO_2$ removal obtained by the ECLA treatment if the current level of ventilation substantially corresponds to, or exceeds, the threshold level of ventilation of the patient. In accordance with this scenario, the threshold level of ventilation may be set below the maximum level of ventilation of the patient in order to optimize the use of the lungs for ventilation while minimizing the risk of injury to the lungs from the ventilator. In this way, the lungs may be provided with optimal ventilation conditions to allow them to heal.

Thus, instead of further intensifying the operation of the ventilator to reduce the $CO_2$ content in the patient's circulatory system, which is the normal response to detection of alarmingly high $CO_2$ production or increase in $CO_2$ production over time during respiratory treatments, the at least one control unit controls the ECLA device to achieve the required $CO_2$ reduction in case the current level of ventilation of the patient is high. Thereby, the ventilation can be maintained at a non-injurious intensity, minimizing the risk of injuring the pulmonary system of the patient, while the $CO_2$ content in the circulatory system of the patient can be maintained at an acceptable level. A non-injurious ventilation intensity may in this context be regarded as a ventilation intensity according to which the tidal volume of breathing gas supplied to the patient does not exceed 6 ml/kg predicted bodyweight, and the peak pressure delivered to the patient does not exceed 30 mbar.

Thus, the proposed coordinated control of the ECLA device and the ventilator ensures that neither the ECLA device nor the ventilator has to be operated at an intensity level which may jeopardize patient safety. Or, in other words, that the intensities of the ECLA treatment and the respiratory treatment can be automatically adjusted to provide effective but yet gentle removal of $CO_2$ from the circulatory system of the patient.

Another advantage is that since the ventilator can be operated to assist the ECLA device in the removal of CO2 from the patient's circulatory system, the extracorporeal blood flow generated by the ECLA device can be reduced as compared to the blood flow normally required for ECLA treatment. While a conventional ECLA device typically operates at flows between 4 and 7 litres per minute, it has been found that flows of 0.5-1.5 l/min or less may be sufficient to maintain the CO2 content in the circulatory system of a patient at an acceptable level when the ECLA device is used in parallel with a ventilator operating at a non-injurious ventilation intensity, even when treating patients suffering from severe lung diseases. This is advantageous in that the cannulae and tubes connecting the ECLA device to the circulatory system of the patient can be made much thinner than normally required when treating solely with ECLA devices, which in turn makes connection of a patient to the ECLA device less critical. While a conventional ECLA device normally is connected between a large vein (e.g. the inferior or superior vena cava) and a large artery (e.g. the aorta), the proposed ECLA device may be connected to the patient through a vein-to-vein connection having a common or two separate connection points. For example, the ECLA device may be connected to the patient through a vein-to-vein connection by means of a double lumen cannula, similar to cannulae commonly used in dialysis.

The bioelectric signal may be any type of measurable bioelectrical signal indicative of the breathing efforts of the patient. Non-exclusive examples of usable bioelectric signals are EMG (electromyogram) signals representing the electrical activity of the diaphragm or muscles in the upper airways (e.g. the laryngopharyngeal region), and EEG (electroencephalography) signals representing the electrical activity of respiratory centres of the brain.

The bioelectric sensor for detecting the bioelectric signal may be any type of bioelectric sensor capable of measuring a bioelectric signal indicative of the breathing efforts of the patient. In an exemplary embodiment, the bioelectric sensor comprises an oesophageal catheter carrying a number of electrodes for capturing EMG signals from the diaphragm and/or upper airways of the patient. An oesophageal catheter configured for detection of diaphragm EMG, i.e., the electrical activity of the diaphragm, is often referred to as an Edi catheter in the field of NAVA ventilation.

The act of controlling the operation of the ECLA device so as to control the degree of CO2 removal achieved through the ECLA treatment may be performed in various ways. For example, the at least one control unit may be configured to control any of, or any combination of, an extracorporeal flow of blood generated by the ECLA device, a flow of fresh gas for extracorporeal blood oxygenation, and a composition of the fresh gas for extracorporeal blood oxygenation, based on the bioelectric signal.

Likewise, the act of controlling the operation of the ventilator so as to control the degree of CO2 removal achieved through the respiratory treatment may be performed in various ways. For example, the at least one control unit may be configured to control any of, or any combination of, a tidal volume of breathing gas delivered to the patient, a peak pressure of breathing gas delivered to the patient, a positive end-expiratory pressure (PEEP) applied to the patient at the end of expiration, a respiratory rate, a composition of the breathing gas delivered to the patient, and a duration of the breaths delivered to the patient, based on the bioelectric signal.

According to another aspect of the present disclosure there is provided a method for CO2 removal from the circulatory system of a patient, comprising the step of controlling the operation of an ECLA device providing ECLA treatment to a patient through extracorporeal removal of CO2 from the patient's blood, so as to control a degree of CO2 removal obtained by the ECLA treatment. The method further comprises the steps of registering a bioelectric signal indicative of the patient's efforts to breathe, and automatically controlling the operation of the ECLA device based on the registered bioelectric signal.

The method may comprise additional steps corresponding to any of, or any combination of, the actions performed by the at least one control unit of the above described system. The method may be performed in and by the ECLA device but may, in some embodiments, be performed in cooperation with a ventilator and/or an external monitor unit, as will be clear from the detailed description following hereinafter.

The method is typically a computer implemented method that is performed or caused by the at least one control unit upon execution of a computer program that is stored in a non-volatile memory of the system.

Consequently, according to another aspect of the present disclosure, there is provided a computer program for CO2 removal from the circulatory system of a patient being connected to a system comprising an ECLA device for providing ECLA treatment to the patient through extracorporeal removal of CO2 from the patient's blood. The computer program comprises computer-readable code segments which, when executed by a processor, causes the at least one control unit of the system to control the ECLA device based on a bioelectric signal detected by the bioelectric sensor.

BRIEF DESCRIPTION OF DRAWINGS

A more complete appreciation of the invention disclosed herein will be obtained as the same becomes better understood by reference to the following detailed description when considered in conjunction with the accompanying drawings briefly described below, in which drawings the same reference numerals are used to represent corresponding functional elements.

DETAILED DESCRIPTION

It is generally assumed that the respiratory drive of a patient is primarily based on the CO2 content in the patient's blood, which in turn depends on the alveolar ventilation of the patient and any extracorporeal removal of CO2 from the patient's blood. Relying on this assumption, the present disclosure suggests using a bioelectric signal, indicative of a patient's respiratory drive, to control the operation of an ECLA device and thus the degree of extracorporeal removal of CO2 obtained by the ECLA device.

Figure 1:
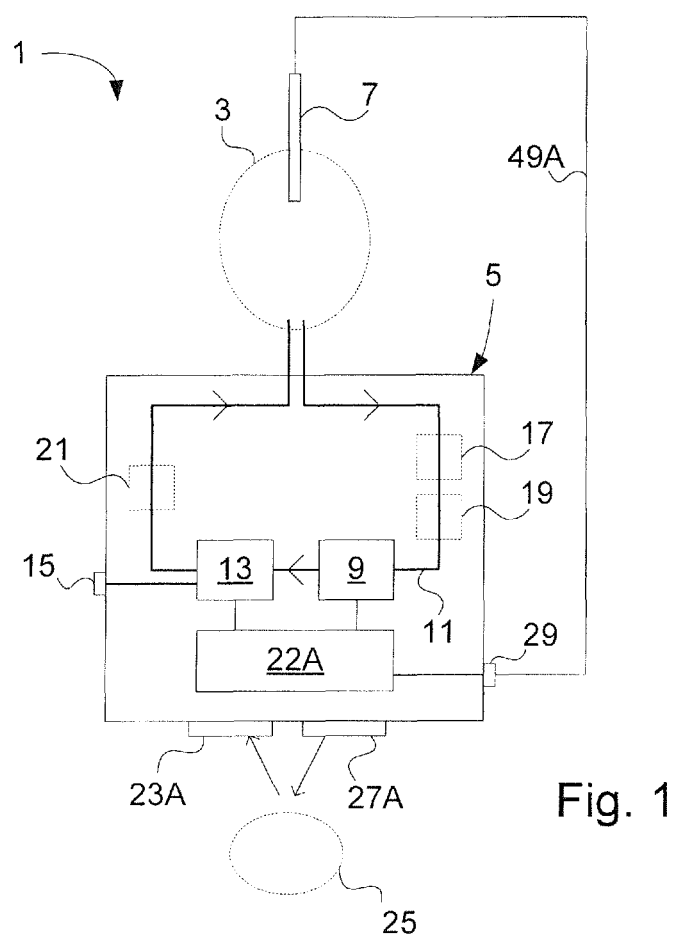
FIG. 1 illustrates a system for CO2 removal from the circulatory system of a patient, according to an exemplary embodiment of the present disclosure.

FIG. 1 illustrates a first exemplary embodiment of a system 1 for CO2 removal from the blood of a patient 3. The system 1 is typically an intensive care system for treatment of critically ill patients.

The system 1 comprises a medical device 5, herein referred to as an extracorporeal lung assist (ECLA) device, for providing ECLA treatment to the patient 3 through extracorporeal removal of CO2 from the patient's blood. The ECLA device 5 may, in some embodiments, constitute what is often referred to as a heart-lung machine or an ECMO machine. The ECLA device 5 is coupled to a bioelectric sensor 7 for registering a bioelectric signal indicative of the respiratory drive of the patient 3, i.e., a bioelectric signal that is indicative of the patient's efforts to breathe, and configured to automatically adjust the degree of CO2 removal obtained by the ECLA treatment based on the bioelectric signal.

The ECLA device 5 is configured to provide ECLA treatment to the patient 3 by generating an extracorporeal flow of blood from the patient 3, oxygenating the blood through extracorporeal gas exchange in which CO2 is removed from, and oxygen (O2) added to, the extracorporeal blood flow, and returning the oxygen-enriched blood to the patient 3.

To generate the flow of blood to and from the patient 3, the ECLA device 3 may comprise a flow generator 9, typically in form of one or several roller, turbine and/or centrifugal pumps. The flow generator 9 generates a flow of blood through tubing forming a blood flow path 11 of the ECLA device 5, in which the blood flows as indicated by arrows in the clockwise direction in the drawing.

Oxygenation of the blood is typically performed by an oxygenator 13, e.g., a bubble oxygenator or a membrane oxygenator, arranged downstream of the flow generating means 9. The oxygenator 13 is connected to an inlet 15 of the ECLA device 5 through which the ECLA device 5 receives a flow of oxygen containing fresh gas from a fresh gas supply (not shown). The oxygenator 13 then facilitates the transfer of gases between the blood and the fresh gas flow, i.e., removes CO2 from the blood and adds oxygen to the blood. The ECLA device 5 may further comprise one or several blood-buffer reservoirs (not shown).

Furthermore, the ECLA device 5 may include a sensor arrangement comprising sensors 17, 19, 21 for obtaining sensor measurements related to the ongoing ECLA treatment of the patient 3, such as the composition of the blood before and/or after removal of CO2, the pressure and/or flow in the blood flow path 11, upstream and/or downstream of the flow generator 9, etc. In this exemplary embodiment, the sensor arrangement comprises a first flow and/or pressure sensor 17 upstream of the flow generator 9 for measuring the flow and/or pressure in the blood flow path 11, a blood gas analyser 19 upstream of the flow generator 9 for measuring the O2 and/or CO2 content of the blood in the blood flow path 11, and a second flow and/or pressure sensor 21 downstream of the flow generator 9 for measuring the flow and/or pressure in the blood flow path 11. The blood gas analyser 19 may be any type of blood gas analyser for determination of O2 and/or CO2 content in blood. For example, the blood gas analyser 19 may be adapted for determination of the O2 and/or CO2 content of blood through chemical and/or optical analysis, e.g., based on measurements relating to any of, or any combination of, the partial pressure of CO2 or O2 in the blood, the pH of the blood, and the colour of the blood. Other components typically included in an ECLA device, such as heat exchangers and temperature sensors, may also be arranged along the gas flow path 11 of the ECLA device 5 but have been omitted in the drawing so as not to obscure the drawing with unnecessary detail.

The sensors 17, 19, 21, the flow generator 9, and the oxygenator 13 are coupled to a control unit 22A of the ECLA device 5, which control unit 22A may be configured to automatically control the flow generator 9 and/or the oxygenator 13 based on sensor data obtained by the various sensors 17, 19, 21. The control unit 22A is also coupled to a user input device 23A, such as a touch screen, keypad or a rotary control knob, and configured to control the flow generator 9 and/or the oxygenator 13 based on user input parameters that are input on the user input device 23A by an operator 25 of the ECLA device 5. Furthermore, the control unit 22A is coupled to a display device 27A, such as a display unit or a touch screen, and configured to display various ECLA device related parameters informing the operator 25 about the ongoing ECLA treatment. An ECLA device related parameter may, for example, be a setting parameter indicative of a current setting of the ECLA device, set by the operator 25 via the user input device 23A, a sensor parameter indicative of a quantity measured by any of the sensors 17, 19, 21 of the ECLA device 5, and/or a calculated parameter calculated by the control unit 22A of the ECLA device 5 based on one or more sensor parameters and/or one or more setting parameters.

For the sake of clarity, how the sensors 17, 19, 21, the flow generator 9, the oxygenator 13, the user input device 23A and the display device 27A are coupled to the control unit 22A is omitted from the drawings. However, the coupling of these components of the system 1 may be provided by an electronic cable or wire, or by a wireless connection, or by a combination thereof.

In addition to the above mentioned sensors 17, 19, 21, the control unit 22A is coupled to the bioelectric sensor 7 via a signalling link 49A to receive the bioelectric signal captured by the bioelectric sensor 7 on a biosignal input port 29 of the ECLA device 5. Instead or in combination with signals from one or more of the above mentioned sensors, the control unit 22A is configured to use the bioelectric signal received from the bioelectric sensor 7 to automatically control the ongoing ECLA treatment provided by the ECLA device 5 in accordance with the need for CO2 removal from the patient's blood, as indicated by the bioelectric signal. This may, for example, be achieved by the control unit 22A by controlling the flow generator 9 and/or the oxygenator 13 based on the bioelectric signal. The degree of CO2 removal may be increased by the control unit 22A by increasing the blood flow generated by the flow generator 9 and/or by increasing the flow of oxygen diffused into the blood flow by the oxygenator 13, whereas the degree of CO2 removal may be decreased by the control unit 22A by decreasing the blood flow generated by the flow generator 9 and/or by decreasing the flow of oxygen discharged into the blood flow by the oxygenator 13.

In some exemplary embodiments, the control unit 22A may be configured to compare the amplitude and/or frequency of the bioelectric signal with a threshold value, and to increase or decrease the degree of CO2 removal based on the result of the comparison. In other exemplary embodiments, the control unit 22A may be configured to determine a trend for the bioelectric signal, i.e., to identify changes in the bioelectric signal over time, and to increase or decrease the degree of CO2 removal based on the determined trend of the bioelectric signal. For example, the control unit 22A may be configured to use the bioelectric signal as a feedback signal and automatically control the degree of CO2 removal achieved through the ECLA treatment to maintain the bioelectric signal at a desired target level.

The control unit 22A may further be configured to display the bioelectric signal, or one or more signals derived from the bioelectric signal, on the display device 27A of the ECLA device 5.

As would be appreciated by the skilled person, most of the above mentioned components of the ECLA device 5 can be omitted or replaced by other components without deviating from the proposed concept of controlling the degree of CO2 removal obtained by means of the ECLA device based on a bioelectric signal indicative of the respiratory drive of the patient 3. For example, the gas analyser 21 may, in some embodiments, be omitted. However, control of the ECLA device 5 based on sensor measurements obtained by the gas analyser 21 may be desired in cases where a bioelectric signal or a sufficiently reliable bioelectric signal is not available on the biosignal input 29. It is therefore contemplated that the ECLA device 5 may be operated in a first mode in which the degree of extracorporeal CO2 removal is controlled based on the bioelectric signal, and a second mode in which the degree of extracorporeal CO2 removal is controlled based on other sensor measurements, such as measurements obtained by the gas analyser 21.

Figure 2:
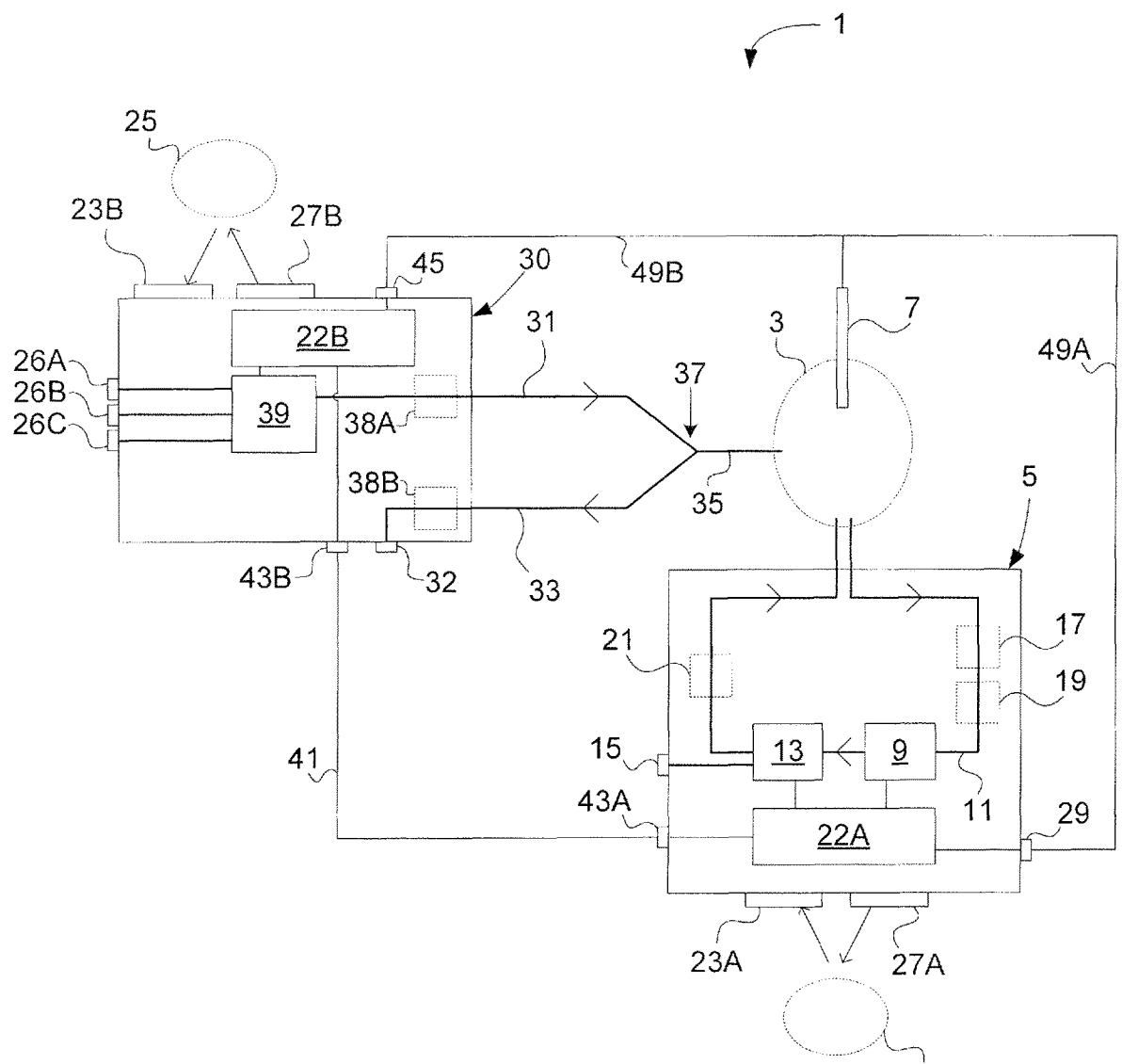
FIG. 2 illustrates a system for CO2 removal from the circulatory system of a patient, according to another exemplary embodiment of the present disclosure

FIG. 2 illustrates another exemplary embodiment of the system 1 for CO2 removal from the blood of a critically ill patient 3. In addition to the components shown in FIG. 1, the system 1 in FIG. 2 is seen to comprise a ventilator 30 for providing respiratory treatment to the patient 3 through the supply of breathing gas to the patient's lungs.

The ventilator 30 is connected to the patient 3 via a patient circuit comprising an inspiratory line 31 for supplying breathing gas to the patient 3, and an expiratory line 33 for conveying expiration gas away from the patient 3 and onto atmosphere or a scavenging system, via a gas outlet 32 of the ventilator. The inspiratory line 31 and the expiratory line 33 are connected to a common line 35, via a so called Y-piece 37, which common line is connected to the patient 3 via a patient connector (not shown), such as a facemask or an endotracheal tube.

The ventilator 30 further comprises a control unit 22B for controlling the ventilation of the patient 3 based on preset parameters and/or measurements obtained by various sensors of the ventilator, such as flow sensors, pressure sensors, gas analysers, etc. In this exemplary embodiment, the ventilator 30 comprises a first pressure and flow sensor arrangement 38A arranged in an inspiratory module of the ventilator, and a second pressure and flow sensor arrangement 38B arranged in an expiratory module of the ventilator 30. The control unit 22B controls the ventilation of the patient 3 by controlling a pneumatic unit 39 for regulating a flow and/or pressure of breathing gas delivered to the patient 3, which pneumatic unit 39 is connected, on the one hand, to one or more gas sources (not shown) via gas inlets 26A-26B and, on the other hand, to the inspiratory line 31. To this end, the pneumatic unit 39 may comprise various gas mixing and regulating means well known in the art of ventilation, such as gas mixing chambers, controllable gas mixing valves, turbines, controllable inspiration valves, etc.

The control unit 22B is also coupled to a user input device 23B, such as a touch screen, keypad or rotary control knob, and configured to control the pneumatic unit 39 based on user input parameters that are input on the user input device 23B by the operator 25. The user input parameters may, for example, include preferred ventilator settings and patient related parameters relating to the patient 3 to be treated. For example, the operator may input information relating to the age, gender and bodyweight of the patient 3, in order for the control unit 22B to automatically adjust the respiratory treatment to an expected physiological state of the patient 3, derived by the control unit 22B based on the patient related parameters. Furthermore, the control unit 22B is coupled to a display device 27B, such as a display unit or a touch screen, and configured to display various ventilator related parameters informing the operator 25 about the ongoing respiratory treatment. A ventilator related parameter may be a setting parameter indicative of a current setting of the ventilator, set by the operator 25 via the user input device 23B, a sensor parameter indicative of a quantity measured by a sensor of the ventilator, and/or a calculated parameter calculated by the control unit 22B of the ventilator 30 based on one or more sensor parameters and/or one or more setting parameters.

The ECLA device 5 and the ventilator 30 are configured to cooperate to provide an effective and non-injurious overall treatment of the patient 3.

For example, in an exemplary mode of operation, the operator 25 may set a desired or maximum level of ventilation for the patient 3 via the user input device 23B of the ventilator 30, e.g., a tidal volume of 6 ml/kg predicted bodyweight. If the bioelectric signal received by the ECLA device 5 indicates a high or increasing respiratory need of the patient 3, assumingly indicating a high or increasing need for removal of CO2 from the patient's blood, the control unit 22B of the ECLA device automatically controls the operation thereof to intensify the ECLA treatment.

Instead of being set by an operator, the desired or maximum level of ventilation of the patient 3 may be automatically determined by the control unit 22B of the ventilator 30, e.g., based on patient related parameters input by the operator 25 via the user input device 23B.

The ECLA device 5 may further be configured to receive information related to the respiratory treatment provided by the ventilator 30, and to automatically adapt the intensity of the ECLA treatment, i.e., the degree of removal of CO2 by the ECLA treatment, based on both the bioelectric signal received from the bioelectric sensor 7 and the information related to the respiratory treatment provided to the patient 3 by the ventilator 30.

The information related to the respiratory treatment may be received by the ECLA device 5 via any type of wired or wireless communication interface. In this exemplary embodiment, the control unit 22A of the ECLA device is communicatively connected to the control unit 22B of the ventilator via wired connection 41. The ECLA device 5 receives the respiratory treatment-related information on a communication port 43A that is connected to a corresponding communication port 43B of the ventilator 30 via the wired connection 41, although in accordance with this disclosure the wired connection 41 may be replaced by a wireless connection.

The information related to the respiratory treatment may advantageously comprise information related to a current level of ventilation of the patient 3 provided by the ventilator 30. The current level of ventilation of the patient 30 may be determined in different ways based on ventilator settings and/or sensor measurements obtained during ventilation, such as pressure and/or flow measurements. Preferably, also patient-related parameters are taken into account in the determination of the current level of ventilation. Typically, the current level of ventilation of the patient 3 is determined based on a tidal volume of breathing gas delivered to the patient 3, a peak pressure of breathing gas delivered to the patient 3, such as a peak airway pressure of the patient, and a bodyweight of the patient 3, e.g., as input by the operator 25 via the user input device 23B of the ventilator 30.

The current level of ventilation of the patient 3 may be compared with a threshold value indicative of a maximum level of ventilation of the patient, whereby the intensity of the ECLA treatment provided by the ECLA device 5 may be controlled based on the bioelectric signal and the result of the comparison.

In the illustrated exemplary embodiment, the ventilator 30 is a bioelectrically controlled ventilator that is controlled based on the same bioelectric signal that is used to control the ECLA device 5. The ventilator 30 is coupled to the bioelectric sensor 7 via a signalling link 49B. The bioelectric signal is received on a biosignal input port 45 of the ventilator 30, and fed to the control unit 22B for further processing and use as control signal for controlling the pneumatic unit 39. For example, the ventilator 30 may be configured to be operated in the well-known mode of NAVA ventilation, in which breathing gas is delivered to the patient 3 in synchrony with and in proportion to the patient's own breathing efforts, as indicated by the bioelectric signal. The NAVA technology is further described in e.g. WO1998/48877, WO1999/62580, WO2006/131149, and WO2008/131798.

The system 1 is preferably configured such that the ECLA device 5 is operated as a slave to the ventilator 30 in a type of master-slave configuration in which $CO_2$ removal is primarily achieved through the respiratory treatment provided by the ventilator 30, and in which ECLA treatment is provided by the ECLA device 5 only if the respiratory treatment is insufficient in order to maintain the level of $CO_2$ in the patient's blood at an acceptable level.

To this end, the control unit 22B of the ECLA device 5 may be configured to control the operation of the ECLA device 5 so as to increase the degree of $CO_2$ removal obtained by the ECLA treatment only when the bioelectric signal indicates that a total degree of $CO_2$ removal obtained by the ECLA treatment and the respiratory treatment is insufficient, and the current level of ventilation substantially corresponds to, or exceeds, the desired or maximum level of ventilation of the patient 3. If, on the other hand, the current level of ventilation is below the maximum level of ventilation, the ECLA treatment may be maintained at a current level of intensity whereby the control unit 22A of the ventilator 30 may be configured to increase the intensity of the respiratory treatment provided by the ventilator 30, e.g., by adjusting the tidal volume of breathing gas delivered to the patient 3, the peak pressure of breathing gas delivered to the patient 3, the PEEP applied to the patient 3 at the end of expiration, the respiratory rate, and/or the duration of the breaths delivered to the patient 3. This allows the ECLA device 5 to be operated at low intensity as long as the bioelectric signal and the current level of ventilation indicate that a sufficient degree of $CO_2$ removal is obtained at a non-injurious level of ventilation.

A configuration in which the ECLA device 5 is operated as a master and the ventilator 30 is operated as slave to the ECLA device 5 is also within the scope of the present disclosure. In such a scenario, the ECLA treatment provided by the ECLA device 30 is the primary means of $CO_2$ reduction from the blood of the patient, whereby the respiratory treatment of the patient, provided by the ventilator 30, is intensified only if the ECLA treatment approaches or exceeds a set maximum ECLA treatment intensity.

It should be understood that the above mentioned functionality for controlling the operation of the ECLA device 5 based on a bioelectric signal indicative of the respiratory drive of a patient may reside in any of, or any combination of, the ECLA device 5, the ventilator 30, and an external unit, such as an external monitoring unit.

Figure 3:
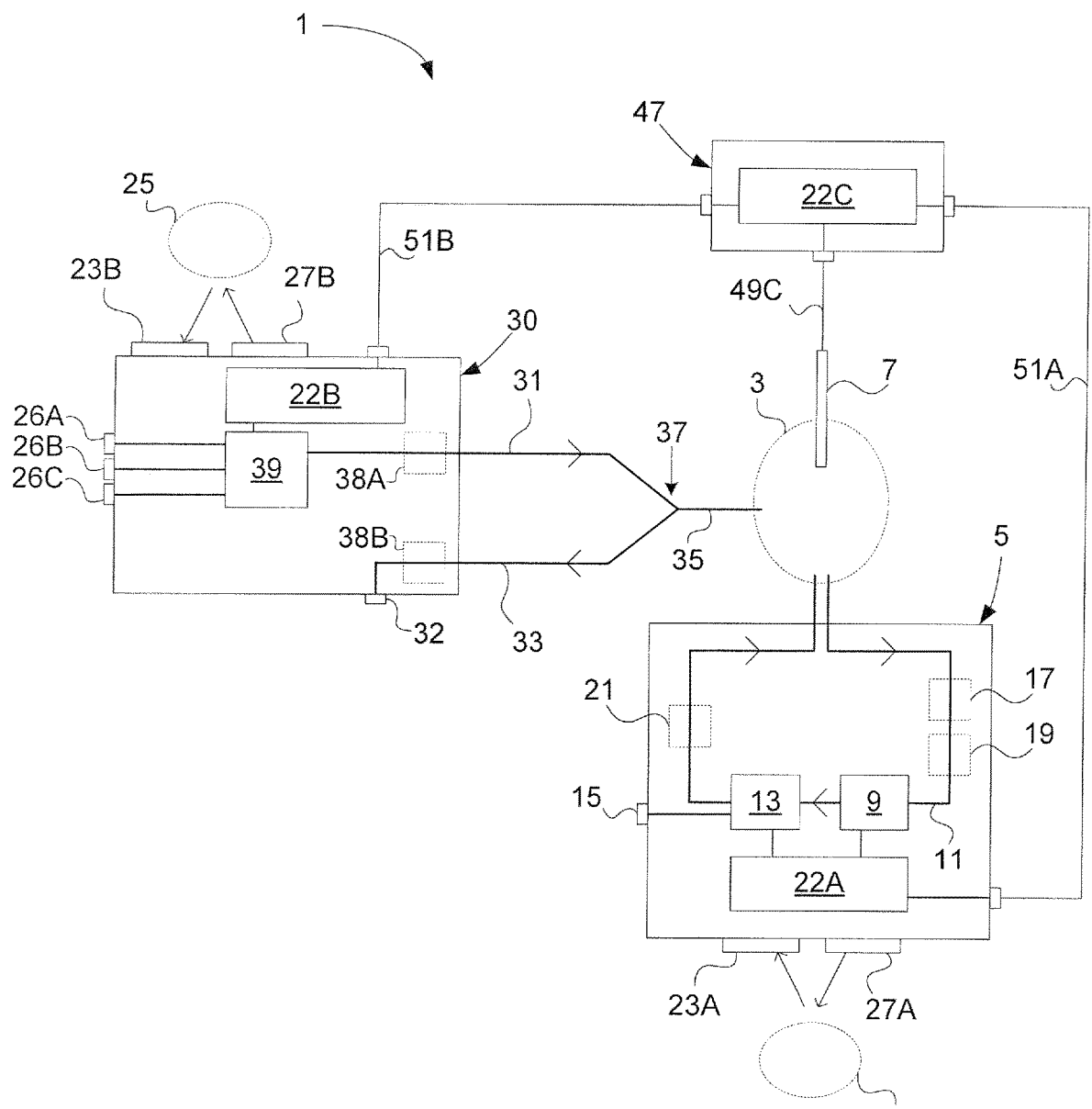
FIG. 3 illustrates a system for CO2 removal from the circulatory system of a patient, according to yet another exemplary embodiment of the present disclosure.

FIG. 3 illustrates an exemplary embodiment of the system 1 in which the bioelectric sensor 7 is coupled to a standalone monitor unit 47 that is configured to control both the ECLA device 5 and the ventilator 30 based on the bioelectric signal captured by the bioelectric sensor 7. The monitor unit 47 may be an Edi monitoring unit as described in WO2016/060596 (reference numeral 1), further adapted to control the operation of the ECLA device 5 in dependence of the bioelectric signal and, preferably, the current level of ventilation provided to the patient 3 by the ventilator 30. To this end, the standalone monitor unit 47 comprises a control unit 22C which alone or in combination with any or both of the control units 22A and 22B provides the above described functionality. The control unit 22C is coupled to the bioelectric sensor 7 via a signalling link 49C and to the control units 22A, 22B of the ECLA device 5 and the ventilator 30 via a respective control link 51A and 51B.

The bioelectric signal used to control the ECLA device 5 in accordance with the principles described herein may be any type of measurable bioelectrical signal indicative of the breathing efforts of the patient 3, such as an EMG signal representing the electrical activity of the diaphragm or muscles in the laryngopharyngeal region of the patient 3, or an EEG signal representing the electrical activity of respiratory centres of the patient's brain.

The bioelectric sensor 7 of the system 1 may hence be any type of bioelectric sensor or sensor arrangement known in the art for detection of bioelectric signals indicative of a subject's effort to breath. For example, the bioelectric sensor 7 could comprise a number of surface electrodes placed on the ribcage, the abdomen or in the vicinity of the phrenic nerve of the patient 3 to sense and filter out diaphragmatic EMG signals to be used in the control of the ECLA device 5 and, optionally, the ventilator 30. According to another example, the bioelectric sensor 7 could be devised to detect laryngopharyngeal EMG signals of the patient 3, and to use the laryngopharyngeal EMG signals for bioelectrical control of the ECLA device 5 and, optionally, the ventilator 30. The bioelectric sensor 7 could, for example, be devised as the bioelectric sensor for detection of laryngopharyngeal EMG signals described in the international patent application WO2016/153406 by the same applicant. According to yet another example, the bioelectric sensor 7 may comprise scalp EEG electrodes for the capturing of EEG signals from the patient's brain.

Figure 4:
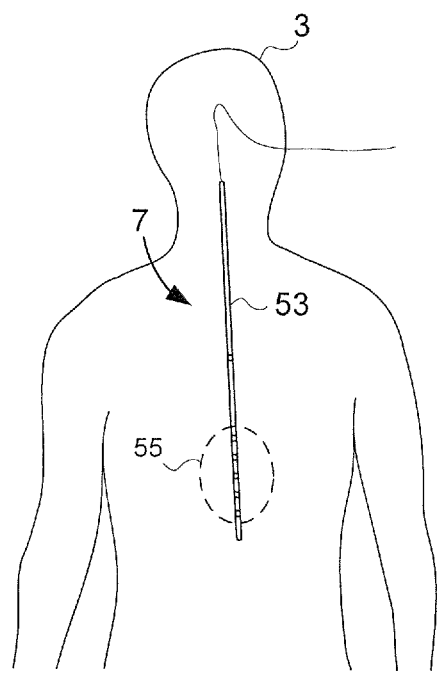
FIG. 4 illustrates a bioelectric sensor for the capturing of a bioelectric signal indicative of the patient's effort to breathe, according to an exemplary embodiment of the present disclosure.

In one exemplary embodiment, illustrated in FIG. 4, the bioelectric sensor 7 is an EMG detector for recording the diaphragm EMG of the patient 3. To this end, the bioelectric sensor 7 comprises an oesophageal catheter 53 for capturing myoelectrical signals (EMG signals) from the diaphragm of the patient 3. The catheter 53 comprises a number of electrodes 55 that produce a number of subsignals which are processed to calculate a resulting signal, the Edi signal, representing the electrical activity of the diaphragm and so indicative of the patient's efforts to breathe. The Edi signal may then be advantageously used to control the ECLA device 5 and, optionally, the ventilator 30 in accordance with the principles described above.

Figure 5:
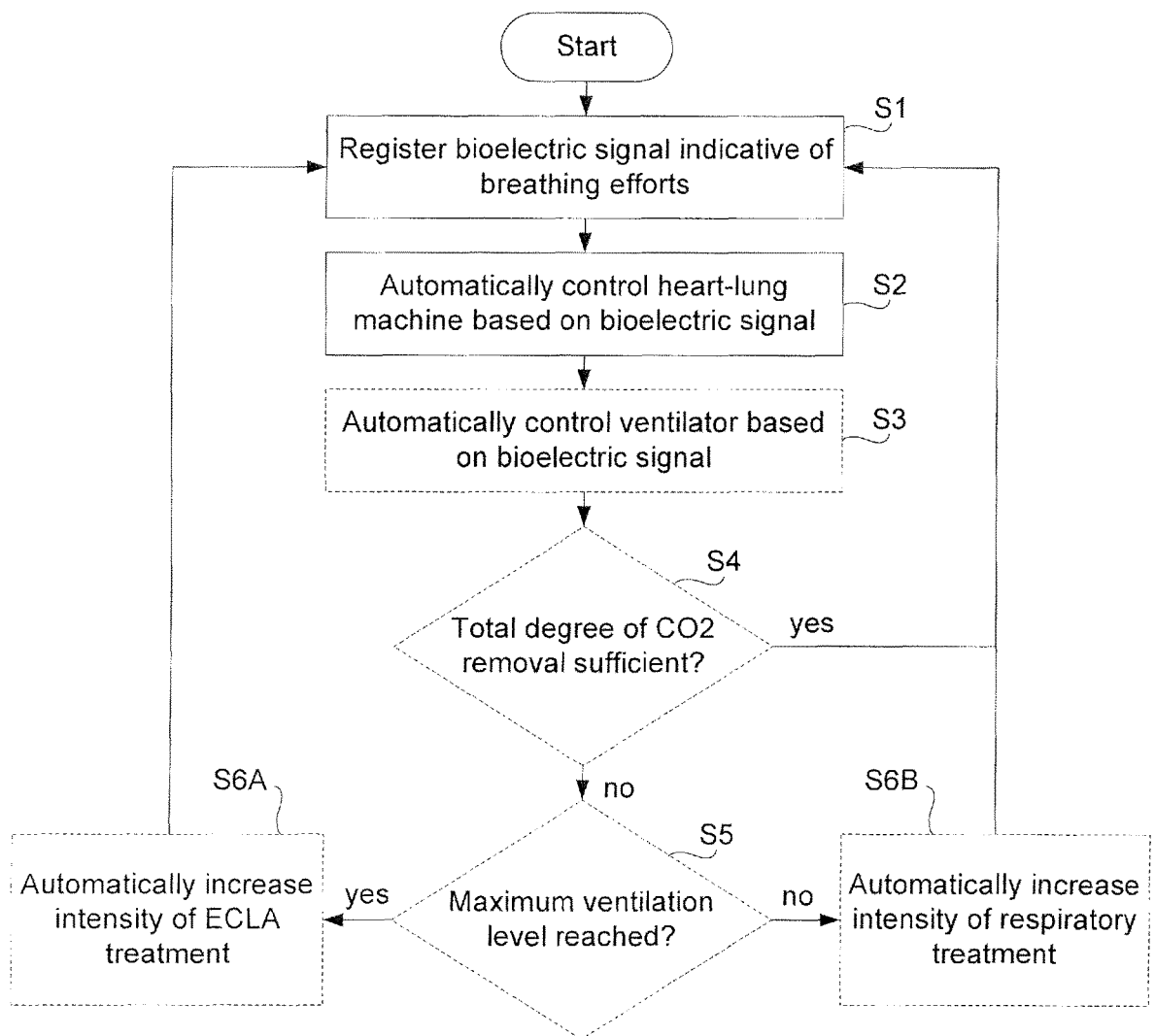
FIG. 5 is a flowchart illustrating a method for CO2 removal from the circulatory system of a patient, according to an exemplary embodiment of the present disclosure.

FIG. 5 is a flow chart illustrating a method for $CO_2$ removal from the circulatory system of a patient, according to an exemplary embodiment of the present disclosure. The method will now be described with simultaneous reference to the system 1 illustrated in FIGS. 1-3.

In a first step S1, a bioelectric signal indicative of the patient's efforts to breathe is registered. The registered bioelectric signal is the bioelectric signal captured by the bioelectric sensor 7, or a signal derived from the bioelectric signal captured by the bioelectric sensor 7.

In a second step S2, the bioelectric signal registered in step S1 is used to automatically control the operation of a ECLA device 5 configured to provide ECLA treatment to the patient 3 through extracorporeal removal of $CO_2$ from the patient's blood.

In a third and optional step, S3, the same bioelectric signal is used to automatically control the operation of a bioelectrically controlled ventilator 30, such as a NAVA-enabled ventilator, configured to provide respiratory treatment to the patient 3 through the supply of breathing gas to the lungs of the patient.

In a fourth and optional step, S4, it is determined from the bioelectric signal whether the total degree of $CO_2$ removal obtained by the ECLA treatment and the respiratory treatment is sufficient. As briefly discussed above, this may be achieved by determining if the amplitude and/or frequency of the bioelectric signal exceed a predetermined threshold value, or if the amplitude and/or frequency of the bioelectric signal increase over time, in which case it can be assumed that the total degree of $CO_2$ removal is insufficient.

If, in step S4, it is determined that the total degree of $CO_2$ removal is sufficient ("yes"), the method returns to step S1. If it is determined that the total degree of $CO_2$ removal is insufficient ("no"), the method proceeds to a fifth and optional step, S5.

In the fifth and optional step, S5, it is determined if a maximum level of ventilation is reached, i.e., if the current level of ventilation provided to the patient 3 by the ventilator 30 equals or exceeds a maximum level of ventilation. The maximum level of ventilation may be input to the ventilator 30 by an operator 25 or automatically determined by the ventilator 30 based on, e.g., patient related parameters, as discussed in more detail above.

If, in step S5, it is determined that the maximum level of ventilation is reached ("yes"), the method proceeds to an optional step S6A. If it is determined that the maximum level of ventilation is not reached ("no"), the method proceeds to an optional step S6B.

In the optional step S6A, the intensity of the ECLA treatment provided by the ECLA device 5 is automatically increased, meaning that the degree of removal of $CO_2$ obtained by the ECLA treatment is increased. As discussed in more detail above, this may, for example, be achieved by increasing an extracorporeal flow of blood generated by the ECLA device 5, increasing a flow of oxygen containing fresh gas that is discharged into the blood flow, and/or increasing the oxygen content of the fresh gas that is discharged into the extracorporeal blood flow.

In the optional step S6B, the intensity of the respiratory treatment provided by the ventilator 30 is automatically increased, meaning that the degree of removal of $CO_2$ obtained by the respiratory treatment is increased. As discussed in more detail above, this may for example be achieved by increasing the tidal volume of breathing gas delivered to the patient, increasing the peak pressure of breathing gas delivered to the patient, increasing the PEEP applied to the patient at the end of expiration, increasing the respiratory rate, and/or decreasing a duration of the breaths delivered to the patient.

The method may be a computer implemented method that is performed or caused to be performed by the at least one control unit 22A, 22B, 22C of the system 1 upon execution of a computer program. To this end, the at least one control unit 22A, 22B, 22C typically includes at least one non-volatile memory storing the computer program, and at least one processor for executing code segments of the computer program. The computer program may reside in its entirety in the control unit 22A of the ECLA device, for example. In other embodiments, the computer program may reside in the control unit 22B of the ventilator 30, or in the control unit 22C of the standalone monitor unit 47. In yet other embodiments, the computer program may be a distributed computer program residing in at least two of the control units 22A, 22B, 22C of the ECLA device 5, the ventilator 30, and the standalone monitor unit 47, respectively, whereby two or all of the ECLA device 5, the ventilator 30 and the standalone monitor unit are configured to cooperate to perform the method.

The invention claimed is:

1. A system for carbon dioxide ($CO_2$) removal from a circulatory system of a patient, comprising:

an extracorporeal lung assist (ECLA) device providing an ECLA treatment to the patient through extracorporeal removal of $CO_2$ from the patient's blood, the ECLA device being configured to generate an extracorporeal flow of blood from the patient, oxygenating the blood through extracorporeal gas exchange in which $CO_2$ is removed from, and oxygen added to, the extracorporeal blood flow;

at least one control unit controlling an operation of the ECLA device so as to control a degree of $CO_2$ removal obtained by the ECLA treatment; and a bioelectric sensor detecting an electromyographic (EMG) signal representing an electrical activity of a diaphragm or muscles in an upper airway of the patient and indicative of efforts of a respiratory drive of the patient, wherein the at least one control unit is configured to control the operation of the ECLA device to adjust the degree of $CO_2$ removal obtained by the ECLA treatment based on the detected EMG signal, wherein the at least one control unit is configured to increase the degree of $CO_2$ removal obtained by the ECLA treatment when one of an amplitude and a frequency of the EMG signal exceeds a predetermined threshold value or increases over time.

2. The system according to claim 1, further comprising:

a ventilator providing respiratory treatment to the patient through a supply of breathing gas to lungs of the patient, wherein the at least one control unit is configured to control the operation of the ECLA device based on the EMG signal and a current level of ventilation of the patient provided by the ventilator.

3. The system according to claim 2, wherein the at least one control unit is configured to determine the current level of ventilation of the patient from (a) a tidal volume and/or a peak pressure currently being delivered to the patient by the ventilator and/or (b) a bodyweight of the patient.

4. The system according to claim 2, wherein the at least one control unit is configured to control the ECLA device so as to increase the degree of $CO_2$ removal obtained by the ECLA treatment when one of the amplitude and the frequency of the EMG signal exceeds the predetermined threshold value or increases over time, and the current level of ventilation substantially corresponds to, or exceeds, one of (a) a predetermined threshold level of ventilation of the patient and (b) a maximum level of ventilation of the patient.

5. The system according to claim 2, wherein the at least one control unit is further configured to control the operation of the ventilator so as to control a degree of CO2 removal obtained by the respiratory treatment based on the EMG signal.

6. The system according to claim 5, wherein the at least one control unit is configured to control the ventilator so as to increase the degree of CO2 removal obtained by the respiratory treatment when one of the amplitude and the frequency of the EMG signal exceeds the predetermined threshold value or increases over time, and the current level of ventilation is below one of (a) a predetermined threshold level of ventilation of the patient and (b) a maximum level of ventilation of the patient.

7. The system according to claim 1, wherein the bioelectric sensor includes an oesophageal catheter carrying a number of electrodes configured to capture the EMG signal from the diaphragm and/or the upper airway muscles of the patient.

8. The system according to claim 1, wherein the at least one control unit is configured to control the operation of the ECLA device by controlling the extracorporeal blood flow generated by the ECLA device, a flow of fresh gas for extracorporeal blood oxygenation, and/or a composition of the fresh gas for extracorporeal blood oxygenation, based on the EMG signal.

9. An extracorporeal lung assist (ECLA) device for providing ECLA treatment to a patient through an extracorporeal removal of carbon dioxide (CO2) from blood of a patient, the ECLA device being configured to generate an extracorporeal flow of blood from the patient, oxygenating the blood through extracorporeal gas exchange in which CO2 is removed from, and oxygen added to, the extracorporeal blood flow, the ECLA device comprising:
a control unit controlling an operation of the ECLA device so as to control a degree of CO2 removal obtained by the ECLA treatment,
wherein the control unit is configured to control the operation of the ECLA device to adjust a degree of CO2 removal obtained by the ECLA treatment based on an electromyographic (EMG) signal representing an electrical activity of a diaphragm or muscles in an upper airway of the patient and indicative of a respiratory drive of the patient, wherein the at least one control unit is configured to increase the degree of CO2 removal obtained by the ECLA treatment when one of an amplitude and a frequency of the EMG signal exceeds a predetermined threshold value or increases over time.

10. A method for carbon dioxide (CO2) removal from a circulatory system of a patient, comprising the step of:
controlling an operation of an extracorporeal lung assist (ECLA) device providing an ECLA treatment to the patient through an extracorporeal removal of CO2 from blood of the patient so as to control a degree of CO2 removal obtained by the ECLA treatment, wherein the ECLA device is configured to generate an extracorporeal flow of blood from patient, oxygenating the blood through extracorporeal gas exchange in which CO2 is removed from, and oxygen added to, the extracorporeal blood flow;
registering an electromyographic (EMG) signal representing an electrical activity of a diaphragm or muscles in an upper airway of the patient and indicative of the respiratory drive of the patient; and
automatically controlling the operation of the ECLA device to adjust the degree of CO2 removal obtained by the ECLA treatment based on the registered EMG signal, wherein automatically controlling the operation of the ECLA device includes increasing the degree of CO2 removal obtained by the ECLA device when one of an amplitude and a frequency of the EMG signal exceeds a predetermined threshold value or increases over time.

11. The method according to claim 10, further comprising the step of:
automatically controlling the operation of the ECLA device based on the EMG signal and a current level of ventilation of the patient, provided by a ventilator providing respiratory treatment to the patient through the supply of breathing gas to the patient's lungs.

12. The method according to claim 11, wherein the current level of ventilation is determined from (a) a tidal volume and/or a peak pressure currently being delivered to the patient by the ventilator and/or (b) a bodyweight of the patient.

13. (Withdrawn, Currently Amended) The method according to claim 11, further comprising the step of:
automatically controlling the ECLA device so as to increase the degree of CO2 removal obtained by the ECLA treatment when one of the amplitude and the frequency of the EMG signal exceeds the predetermined threshold value or increases over time, and the current level of ventilation substantially corresponds to, or exceeds, one of (a) a predetermined threshold level of ventilation of the patient and (b) a maximum level of ventilation of the patient.

14. The method according to claims 11, further comprising the step of:
automatically controlling the operation of the ventilator so as to control a degree of CO2 removal obtained by the respiratory treatment based on the EMG signal.

15. The method according to claim 14, further comprising the step of:
automatically controlling the ventilator so as to increase the degree of CO2 removal obtained by the respiratory treatment when one of the amplitude and the frequency of the EMG signal exceeds the predetermined threshold value or increases over time, and the current level of ventilation is below one of (a) a predetermined threshold level of ventilation of the patient and (b) a maximum level of ventilation of the patient.

16. The method according to claim 10, wherein the operation of the ECLA device is controlled by controlling the extracorporeal blood flow generated by the ECLA device, a flow of fresh gas for extracorporeal blood oxygenation, and/or a composition of the fresh gas for extracorporeal blood oxygenation based on the EMG signal.

* * * * *